United States Patent
Lagun et al.

(10) Patent No.: US 10,127,680 B2
(45) Date of Patent: Nov. 13, 2018

(54) EYE GAZE TRACKING USING NEURAL NETWORKS

(71) Applicant: GOOGLE LLC, Mountain View, CA (US)

(72) Inventors: Dmitry Lagun, San Jose, CA (US); Vidhya Navalpakkam, Santa Clara, CA (US)

(73) Assignee: Google LLC, Mountain View, CA (US)

(*) Notice: Subject to any disclaimer, the term of this patent is extended or adjusted under 35 U.S.C. 154(b) by 0 days.

(21) Appl. No.: 15/195,942

(22) Filed: Jun. 28, 2016

(65) Prior Publication Data

US 2017/0372487 A1    Dec. 28, 2017

(51) Int. Cl.
| | |
|---|---|
| *G06K 9/60* | (2006.01) |
| *G06T 7/33* | (2017.01) |
| *G06T 7/11* | (2017.01) |
| *G06F 3/01* | (2006.01) |
| *G06N 3/04* | (2006.01) |

(52) U.S. Cl.
CPC ............. *G06T 7/33* (2017.01); *G06F 3/013* (2013.01); *G06T 7/11* (2017.01); *G06N 3/0454* (2013.01); *G06T 2207/20084* (2013.01); *G06T 2207/30201* (2013.01)

(58) Field of Classification Search
CPC .......... G06T 2207/20084; G06F 3/013; G06K 9/00604; G06K 9/0061; A61B 3/113; A61B 3/0091
See application file for complete search history.

(56) References Cited

U.S. PATENT DOCUMENTS

| | | |
|---|---|---|
| 2007/0011609 A1 | 1/2007 | Adjouadi et al. |
| 2014/0145935 A1 | 5/2014 | Sztuk et al. |

FOREIGN PATENT DOCUMENTS

| | | |
|---|---|---|
| WO | 1999/26126 | 5/1999 |
| WO | 2014/061017 | 4/2014 |

OTHER PUBLICATIONS

Zhang et al., "Appearance-Based Gaze Estimation in the Wild", CVPR2015, Computer Vision Foundation, 2015, pp. 4511-4520. (Year: 2015).*
International Search Report and Written Opinion issued in International Application No. PCT/US2017/039651, dated Sep. 6, 2017, 14 pages.

(Continued)

*Primary Examiner* — Brian Werner
(74) *Attorney, Agent, or Firm* — Fish & Richardson P.C.

(57) ABSTRACT

Methods, systems, and apparatus, including computer programs encoded on computer storage media, for gaze position prediction using neural networks. One of the systems includes a neural network comprising one or more neural network layers, wherein the neural network is configured to obtain a collection of input facial images of a user, wherein the collection of input facial images of the user comprises (i) a query image of the user, (ii) one or more calibration images of the user, and (iii) a respective calibration label that labels a known gaze position of the user for each of the one or more calibration images of the user; and process the received collection of input facial images of the user using the one or more neural network layers to generate a neural network output that characterizes a gaze position of the user in the query image.

19 Claims, 5 Drawing Sheets

(56) References Cited

OTHER PUBLICATIONS

Bleicher, "Eye-Tracking Software Goes Mobile," IEEE Spectrum, Apr. 23, 2013 [retrieved on Jul. 15, 2016]. Retrieved from the Internet: URL<http://spectrum.ieee.org/computing/software/eyetracking-software-goes-mobile>, 2 pages.
Demjén et al., "Eye Tracking Using Artificial Neural Networks for Human Computer Interaction," Physiol. Res. 60(5):841-844, Aug. 2011.
Pomerleau et al., "Non-Intrusive Gaze Tracking Using Artificial Neural Networks," AAAI Technical Report FS-93-04, pp. 153-156, 1993.
Pomplun et al., "An Artificial Neural Network for High Precision Eye Movement Tracking," KI-94: Advances in Artificial Intelligence, vol. 861 of the series Lecture Notes in Computer Science, pp. 63-69, Jun. 2005.
Sesin et al., "Adaptive eye-gaze tracking using neural-network-based user profiles to assist people with motor disability," Journal of Rehabilitation Research & Development, 45(6):801-818, 2008.
Abdel-Hamid et al., "Convolutional Neural Networks for Speech Recognition," IEEE/ACM Transactions on Audio, Speech, and Language Processing, 2014, 22(10):1-13.

* cited by examiner

EYE GAZE TRACKING USING NEURAL NETWORKS

BACKGROUND

This specification relates to processing inputs through the layers of a neural network to generate outputs.

Neural networks are machine learning models that employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters.

SUMMARY

In general, one innovative aspect of the subject matter described in this specification can be embodied in a gaze prediction system for processing a collection of input facial images of a user to generate a system output that predicts a gaze position of the user, the gaze prediction system comprising: a neural network comprising one or more neural network layers, wherein the neural network is configured to: obtain a collection of input facial images of the user, wherein the collection of input facial images of the user comprises (i) a query image of the user, (ii) one or more calibration images of the user, and (iii) a respective calibration label that labels a known gaze position of the user for each of the one or more calibration images of the user; and process the received collection of input facial images of the user using the one or more neural network layers to generate a neural network output that characterizes a gaze position of the user in the query image.

Other embodiments of this aspect include corresponding computer systems, apparatus, and computer programs recorded on one or more computer storage devices, each configured to perform the actions of the methods. A system of one or more computers can be configured to perform particular operations or actions by virtue of software, firmware, hardware, or any combination thereof installed on the system that in operation may cause the system to perform the actions. One or more computer programs can be configured to perform particular operations or actions by virtue of including instructions that, when executed by data processing apparatus, cause the apparatus to perform the actions.

The foregoing and other embodiments can each optionally include one or more of the following features, alone or in combination. In some implementations the gaze prediction system further comprises an image collection system configured to obtain the collection of input facial images of the user.

In some implementations the gaze prediction system is implemented on a user device, wherein the user device comprises (i) a display screen, and (ii) a front-facing camera.

In some implementations the image collection system obtains the query image of the user using the front facing camera.

In some implementations obtaining the one or more calibration images of the user comprises: determining a size of the display screen; dividing the display screen into a plurality of regions; and for each region: displaying a visible marker in a position within the region of the display screen; obtaining an image using the front facing camera whilst the visible marker is displayed in the position within the region of the display screen.

In some implementations displaying a visible marker in a position within the region of the display screen comprises assigning the position within the region according to a predetermined probability distribution.

In some implementations the system further extracts a facial region of the obtained image to obtain the calibration image.

In some implementations extracting a facial region of the obtained image comprises selecting an eye region of the obtained image.

In some implementations the image collection system is configured to: determine whether the obtained image is noisy; and in response to determining that the obtained image is noisy, reject the obtained image.

In some implementations the generated a neural network output that characterizes the gaze position characterizes the gaze position of the user of the user in the query image as a position on the display screen of the user device.

In some implementations the one or more calibration images of the user comprises nine calibration images of the user.

In some implementations the neural network comprises: a first neural network comprising one or more convolutional layers; a second neural network comprising one or more fully connected layers; wherein the first neural network is configured to: obtain the collection of input facial images of the user; process the collection of input facial images of the user using the one or more convolutional layers to generate a first neural network output; and provide the generated first neural network output to the second neural network, wherein the second neural network is configured to: receive the generated first neural network output; process the generated first neural network output using the one or more fully connected layers to generate the neural network system output that characterizes a gaze position of the user in the query image.

In some implementations the second neural network comprises two or more fully connected layers configured to: receive the generated first neural network output; process the generated first neural network output to generate a pair embedding output, wherein the pair embedding output comprises a similarity measure between each of a respective calibration image and the query image.

In some implementations the second neural network comprises a fully connected layer that is configured to: receive the generated pair embedding output; process the generated pair embedding output to generate an aggregated embedding output, wherein the aggregated embedding output comprises, for each calibration image, a multiplication between a respective calibration image and a pair embedding output.

In some implementations the second neural network comprises a fully connected output layer that is configured to: receive the aggregated embedding output; process the aggregated embedding output to generate the system output that characterizes a gaze position of the user in the query image.

The subject matter described in this specification can be implemented in particular embodiments so as to realize one or more of the following advantages.

Commercial gaze prediction systems are costly and require time and resource consuming training procedures in order accurately predict a gaze position of a particular user. For example, existing gaze prediction systems often require large, impractical amounts of personalized training data to achieve acceptable levels of prediction accuracy. In addition, in some cases the personalized training data may become over fitted and lead to a reduction in accuracy and efficiency of the gaze prediction system. Furthermore, such large amounts of personalized data can often be noisy, e.g., including training data images where a user has their eyes closed or are looking at something other than a calibration gaze point since standard personalized data generation tasks can be monotonous. Noisy personalized data can decrease the computational efficiency of a gaze prediction system, and/or decrease the accuracy of a gaze prediction system.

The gaze prediction system described in this specification requires fewer computational resources, is financially cheaper, scalable, and may achieve equal or higher levels of accuracy compared to other gaze prediction systems. The gaze prediction system described in this specification trains an image recognition system, e.g., a neural network, to predict or otherwise characterize a gaze position of a user in an input query image using a diverse training data set, e.g., including training data from hundreds of users, enabling the image recognition system to achieve high levels of prediction accuracy whilst avoiding the problem of over fitted personalized training data. The training data may include short calibration tasks for multiple users, decreasing the likelihood that the training data includes noisy data and thus improving the computational efficiency and accuracy of the gaze prediction system.

At runtime, the gaze prediction system described in this specification processes a received query image of a user together with a small number of calibration images in order to characterize a gaze position of the user in the received query image. By performing such an online calibration procedure with each received query image, the gaze prediction system described in this specification effectively utilizes available personalized data to achieve higher levels of computational efficiency compared to other gaze prediction systems that require extensive personalized training. Furthermore, due to the online calibration procedure, the gaze prediction system described in this specification may not require subsequent or regular retraining or fine tuning procedures. In addition, the gaze prediction system described in this specification provides off-the-shelf eye tracking using a front facing camera of a user device in which it is used.

The gaze prediction system described in this specification may require less computational resources than other gaze prediction systems and may therefore be implemented as an end to end prediction system on a user device, e.g., a mobile phone or tablet computer. Understanding user attention or predicting gaze positions of a user using a user device has important and far reaching applications. For example, the gaze prediction system described in this system may be used as part of a facial authentication procedure, e.g., to unlock a screen on a user device—thus improving security aspects of the user device.

The gaze prediction system described in this specification may be used and applied in a variety of settings, including hands-free or gaze-based gaming or to assist in eye tracking research in areas such as human-computer interaction, market research or user experience research. Furthermore, the gaze prediction system described in this specification provides increased accessibility for user devices compared to devices that do not run the gaze prediction system described in this specification.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes an off-the-shelf, scalable system and method for using a front facing camera of a user device to predict an eye gaze position of a user. The system is an end-to-end system that obtains a collection of facial images of a user including a query image and one or more calibration images, and processes the collection of facial images to characterize a gaze position of the user as a position on a display screen of the user device.

Figure 1A:
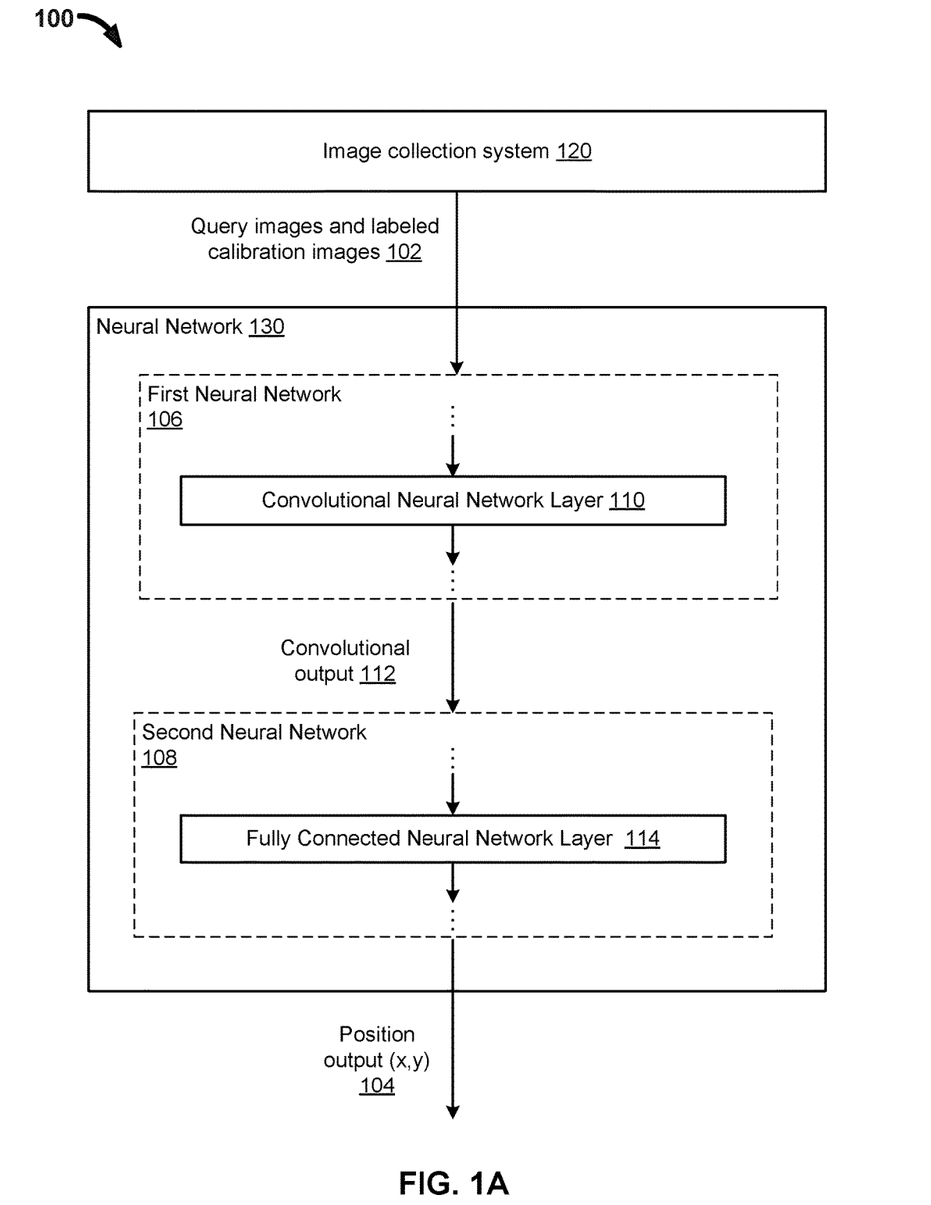
FIG. 1A shows an example gaze prediction system.

FIG. 1A shows an example gaze prediction system 100. The gaze prediction system 100 is an example of a system implemented as computer programs on one or more computers in one or more locations, in which the systems, components, and techniques described below can be implemented. Some or all of the components of the gaze prediction system 100 may be implemented by a user device, e.g., a mobile phone, smart phone, tablet computer, wearable computing device, laptop computer, desktop computer or other portable or stationary computing device, that features a display screen and a front facing camera. In some implementations the gaze prediction system 100 may be implemented in a single user device, e.g., a mobile phone, smart phone or tablet.

The gaze prediction system 100 may include an image collection system 120 and includes a neural network 130. The image collection system 120 may be configured to obtain a collection of input facial images of a user. For example, in implementations where the gaze prediction system 100 is implemented by a user device, the image collection system 120 may obtain a collection of input facial images of a user by causing a camera on the user device to obtain the input facial images. In other implementations, the image collection system 120 may obtain a collection of input facial images of a user by causing the user device to obtain the collection of input facial images using a camera on the user device and transmit the obtained collection of input facial images to the gaze prediction system, e.g., over a communication network. The collection of input facial images of the user includes (i) a query image of the user, e.g., an image in which a prediction of the user's gaze position is to be determined, (ii) one or more calibration images of the user, and (iii) a respective calibration label that labels a known gaze position of the user for each of the one or more calibration images of the user. In some implementations a known gaze position of a user for a calibration image may include a gaze position at which it is expected or predicted that a user is looking. Obtaining one or more calibration images of a user is described in more detail below with reference to FIG. 3.

The neural network 130 is configured to receive a collection of input facial images of a user, e.g., query images and labeled calibration images 102, and to generate a neural network output that characterizes a respective gaze position of the user 104 based on the input. In some implementations the neural network 130 receives a collection of input facial images of a user from an image collection system, e.g., image collection system 120.

The neural network 130 includes multiple neural network layers. Each of the neural network layers in the neural network 130 is configured to receive a respective layer input and process the layer input to generate a respective layer output from the input. The neural network layers collectively process neural network inputs received by the neural network 100 to generate a respective neural network output for each received neural network input.

Some or all of the layers of the neural network 130 are associated with a respective set of parameters. The neural network layers generate outputs from inputs in accordance with the current values of the parameters for the neural network layer. For example, some layers may multiply the received input by a respective parameter matrix of current parameter values as part of generating an output from the received input.

The neural network 130 includes a first neural network 106 and a second neural network 108. The first neural network 106 includes one or more convolutional neural network layers, e.g., convolutional neural network layer 110. A convolutional neural network layer is a neural network layer whose neurons, or nodes, are logically arranged in a three dimensional array: width, height and depth. Neurons inside a convolutional neural network layer are connected to a small region of the layer preceding the convolutional neural network layer, called a receptive field, and each neuron inside a convolutional neural network layer detects the same feature, constituting the property of translation invariance. Typically a local connectivity pattern between neurons of adjacent layers is enforced. Example convolutional neural network layers are described in more detail in "Convolutional Neural Networks for Speech Recognition" Ossama Abdel-Hamid, Abdel-rahman Mohamed, Hui Jiang, Li Deng, Gerald Penn, and Dong Yu, *IEEE/ACM TRANSACTIONS ON AUDIO, SPEECH, AND LANGUAGE PROCESSING, VOL. 22, NO. 10, OCTOBER 2014*.

The first neural network 106 is configured to obtain a collection of input facial images of a user, e.g., query images and labeled calibration images, process the collection of input facial images of the user using one or more convolutional neural network layers, e.g., convolutional neural network layer 110 to generate a first neural network output, e.g., convolutional neural network output 112, and provide the generated first neural network output to the second neural network 108.

Although only one convolutional neural network layer 110 is depicted in FIG. 1 for convenience, the first neural network 106 may include multiple convolutional neural network layers. The number of convolutional neural network layers included in the first neural network 106 may depend on the input to the neural network 130 (or equivalently the input to the first neural network 106).

The second neural network 108 includes one or more fully connected neural network layers, e.g., fully connected neural network layer 114. Although only one fully connected neural network layer 114 is depicted in FIG. 1 for convenience, the second neural network 108 may include multiple fully connected neural network layers. The number of fully connected layers included in the second neural network may depend on a number or quality of input facial images that the neural network is configured to receive. A fully connected neural network layer is a neural network layer who neurons, or nodes, have full connections to all neural network activations in a previous and subsequent neural network layer. Fully connected neural network outputs, may be computed using matrix multiplication followed by a bias offset and activation function.

The second neural network 108 is configured to receive a generated first neural network output, e.g., convolutional neural network output 112, and process the generated first neural network output using the one or more fully connected layers to generate the neural network system output that characterizes a gaze position of the user in the query image, e.g., position output 104. An example second neural network is described in more detail below with reference to FIG. 1B. In some implementations the generated output that characterizes a gaze position of a user in the query image, e.g., position output 104, characterizes the gaze position of the user of the user in the query image as a position on the display screen of the user device. For example, the gaze prediction system 100 may determine a size of the display screen of the user device, assign a horizontal x axis and vertical y axis with a corresponding origin position, e.g., a lower left corner of the user device, and generate a position output (x,y) representing the gaze position of the user on the user device. As another example, the generated output may include a position output in normalized coordinates, which may allow for system outputs to generalize to different user device screen sizes. In some cases, the gaze prediction system 100 may determine a screen resolution of a user device and convert the generated position output to pixel coordinates.

The neural network 130 can be trained on training data that includes multiple training examples in order to determine trained values of the parameters of the neural network layers, i.e., to adjust the values of the parameters from initial values to trained values. For example, during the training, the neural network 130 can process training collections of query images generate a respective neural network output for each training query image. The neural network outputs can then be used to adjust the values of the parameters of the neural network 130. In some implementations the neural network 130 adjusts the values of the parameters using gradient descent and back-propagation neural network training techniques. Training a neural network 130 for gaze prediction is described in more detail below with reference to FIG. 4.

Once the neural network 130 has been trained, the neural network 130 may receive a new neural network input for processing and process the neural network input through the neural network layers to generate a new neural network output for the input in accordance with the trained values of the parameters of the neural network 130.

Figure 1B:
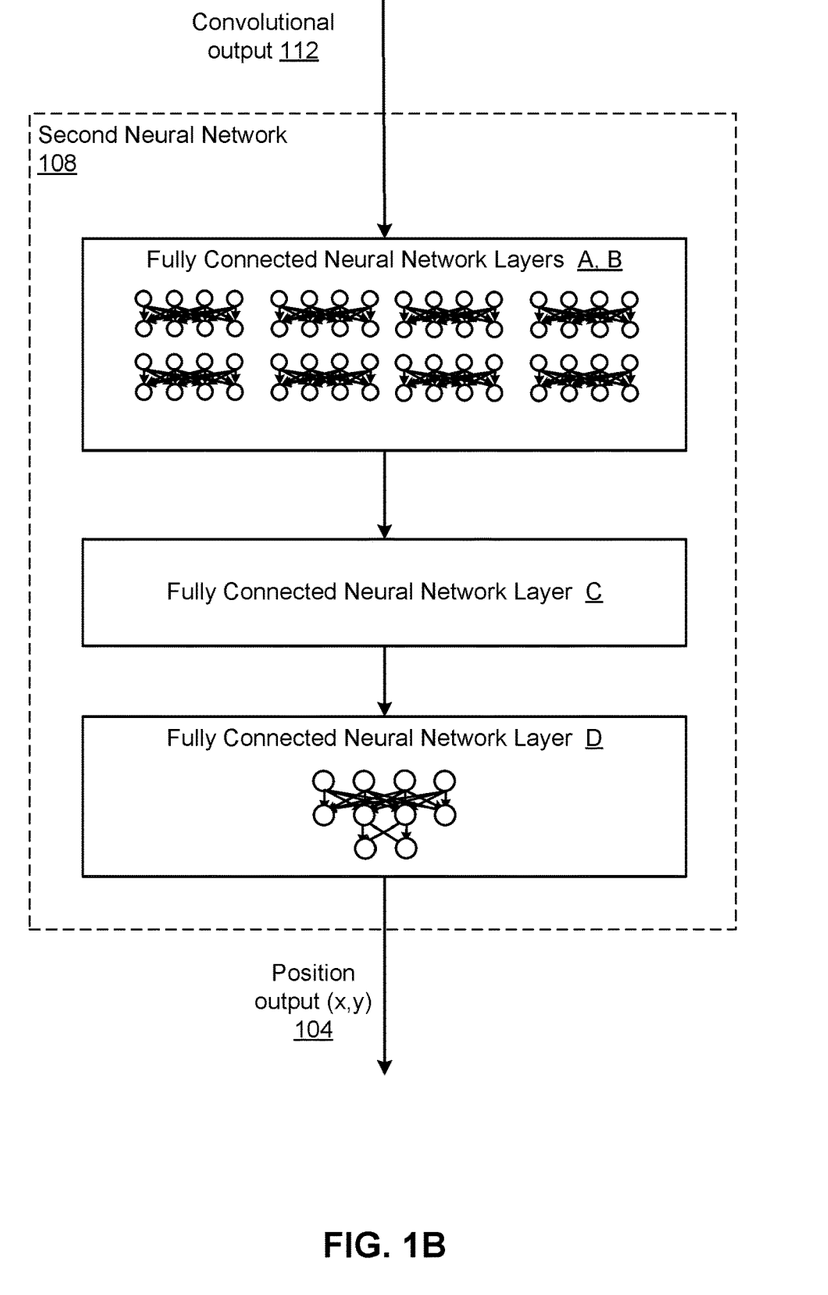
FIG. 1B shows an example neural network.

FIG. 1B shows an example second neural network 108. As described above with reference to FIG. 1A, the second neural network 108 includes one or more fully connected neural network layers. For example, in some implementations the second neural network 108 may include two fully connected layers A and B that are configured to receive the generated first neural network output, e.g., convolutional neural network output 112, and to process the generated first neural network output to generate one or more pair embedding outputs. Each pair embedding output includes a similarity measure between each of a respective calibration image and the query image. The similarity between a query image and a calibration image may be computed based on the output from second neural network 108, e.g., an embedding vector, by taking the difference between two embedding vectors, e.g., a query image embedding vector for the query image and a calibration embedding vector for the calibration image. The query image and calibration image may be determined as similar to one another if components of a vector representing the difference between the corresponding embedding vectors are mostly equal to or close to zero. In this case, the second neural network 108 may output a gaze prediction that is close to the gaze position for the calibration image. The query image and calibration image may be determined as not similar to one another if the components of the vector representing the difference between the corresponding embedding vectors are large. In this case the second neural network 108 may use information from other calibration points that is more similar to the query image.

In addition, in some implementations the second neural network 108 may further include a fully connected layer C that is configured to receive generated pair embedding outputs, as described above, and to process the generated pair embedding outputs to generate an aggregated embedding output. An aggregated embedding output may be obtained by concatenating labels for the calibration images and multiplying pair embeddings with labels of a corresponding image. For example, suppose x1, y1, x2, y2 represent gaze position labels for two calibration points. A pair embedding between a query image and calibration image (q, c1) may be represented by [d1_1, d1_2, d1_3], and a pair embedding (q, c2) may be represented by [d2_1, d2_2, d2_3], where the dimensionality of the embedding is 3, for example. An aggregated embedding layer may then be given by given by: [x1, y1, d1_1*x1, d1_2*x1, d1_3*x1, d1_1*y1, d1_2*y1, d1_3*y1, x2, y2, d2_1*x2, d2_2*x2, d2_3*x2, d2_1*y2, d2_2*y2, d2_3*y2].

Furthermore, in some implementations the second neural network 108 may further include one or more fully connected output layers, e.g., fully connected output layer D, that is configured to receive an aggregated embedding output and process the aggregated embedding output to generate the neural network output that characterizes a gaze position of the user in the query image, e.g., position output 104. For example, to obtain a gaze position prediction, the aggregated embedding layer may be fed into fully connected output layer D, with the last layer having an endpoint of dimensionality equal to 2 for position coordinates (x,y).

Figure 2:
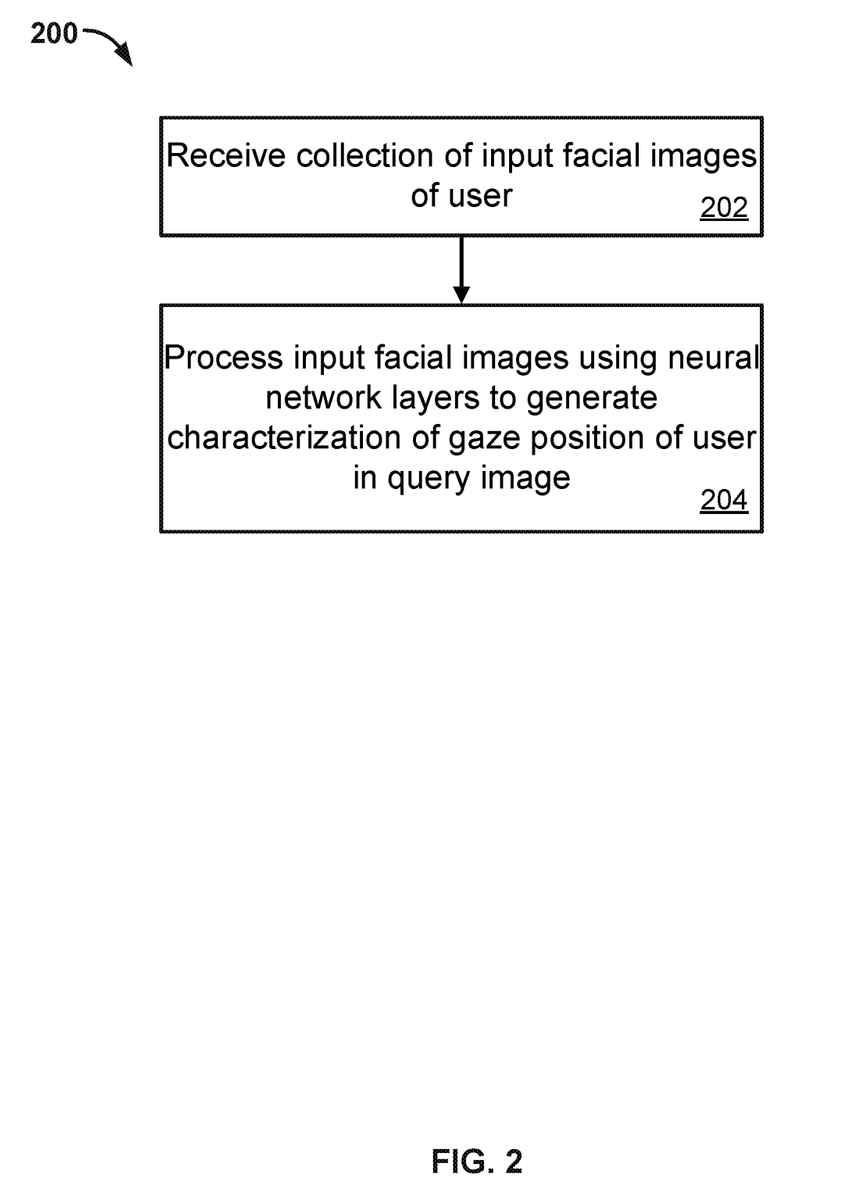
FIG. 2 is a flow diagram of an example process for characterizing a gaze position of a user in a query image.

FIG. 2 is a flow diagram of an example process 200 for characterizing a gaze position of a user in a query image. For convenience, the process 200 will be described as being performed by a system of one or more computers located in one or more locations. For example, a gaze prediction system, e.g., the gaze prediction system 100 of FIG. 1, appropriately programmed in accordance with this specification, can perform the process 200.

The system receives a collection of input facial images of the user (step 202). The collection of input facial images of the user includes (i) a query image of the user, (ii) one or more calibration images of the user, and (iii) a respective calibration label that labels a known gaze position or region of the user for each of the one or more calibration images of the user. In some implementations the one or more calibration images of the user comprises nine calibration images of the user.

In some implementations the process 200 for characterizing a gaze position of a user in a query image may be performed by a gaze prediction system installed on a user device that includes (i) a display screen, and (ii) a front-facing camera, e.g., a cellular phone or tablet. In these cases, the system may obtain the collection of input facial images of the user using a front facing camera. Obtaining one or more calibration images using an image collection system is described in more detail below with reference to FIG. 3.

The system processes the received collection of input facial images of the user using a neural network to generate a neural network output that characterizes the gaze position of the user in the query image (step 204). The neural network may have been trained on multiple training examples to characterize a gaze position of a user in a query image. Training a neural network for gaze prediction is described in more detail below with reference to FIG. 4.

In some implementations the generated a neural network output that characterizes the gaze position characterizes the gaze position of the user of the user in the query image as a position on the display screen of the user device, e.g., directly on the display screen of the user device.

Figure 3:
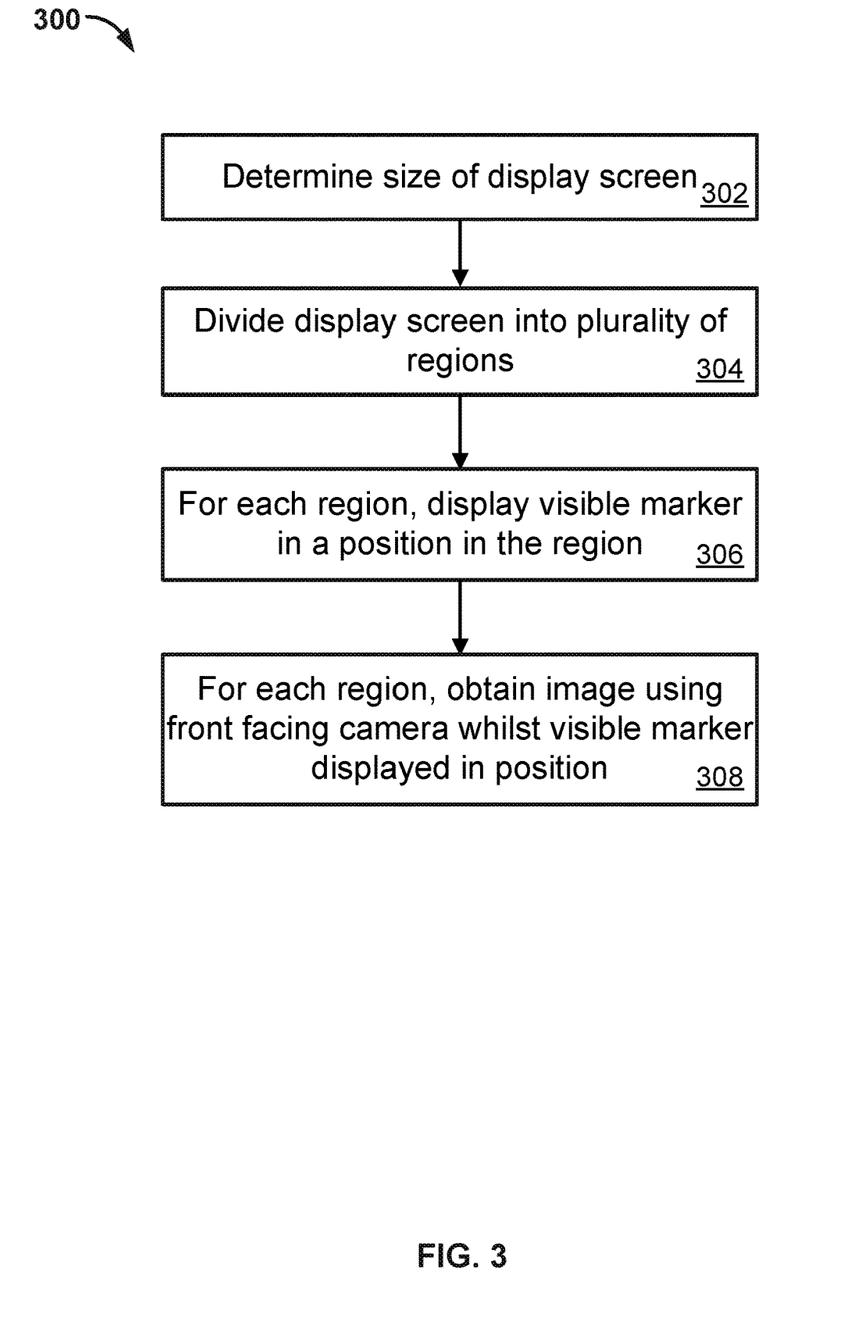
FIG. 3 is a flow diagram of an example process for obtaining one or more calibration images of a user.

FIG. 3 is a flow diagram of an example process 300 for obtaining one or more calibration images of a user using a user device. For convenience, the process 300 will be described as being performed by a system of one or more computers located in one or more locations. For example, an image collection system, e.g., the image collection system 120 of FIG. 1, appropriately programmed in accordance with this specification, can perform the process 300.

The system determines a size of a display screen of the user device (step 302).

The system divides the display screen into multiple regions (step 304). For example, the system may divide the display screen into nine equally sized regions.

For each of the multiple regions, the system displays a visible marker in a position within the region of the display screen (step 306). In some implementations the system may randomly sample a position within a region of the display screen according to a predetermined probability distribution. For example, the system may assign a probability distribution, e.g., two-dimensional Gaussian distribution, to each region of the display screen and sample a position within the region accordingly. In other implementations the system may assign a fixed position within the region of the display screen, e.g., a position that is the center of the region of the display screen.

For each of the multiple regions, the system obtains a respective image using a front facing camera on the user device whilst the visible marker is displayed in the position within the region of the display screen (step 308). For example, the system may display a visible marker in a position within a region of the display screen and obtain an image using a front facing camera on the user device under the assumption that the user of the user device is looking at the visible marker as the image is obtained. In some implementations the system may prompt the user via a notification on the user device to look at the visible marker before obtaining an image using the front facing camera.

In some implementations the system extracts a facial region of the obtained image to obtain the calibration image, e.g., using a facial recognition application implementing standard facial recognition methods included in the gaze prediction system or otherwise running on the user device. In some implementations the system may further select an eye region of the obtained image using standard computer vision techniques.

Optionally, the system may determine whether each image obtained in step 308 is noisy, e.g., whether the image shows a user looking at a position on the display screen, whether the user has their eyes open or closed, whether the system has successfully extracted a facial region, or whether the quality of the image is sufficient using standard computer vision techniques, e.g., face or eye detection application programming interfaces. In response to determining that the obtained image is not noisy, the system accepts the image as a calibration image. In response to determining that the obtained image is noisy, the system rejects the obtained image. The system may obtain a second image to replace the rejected image by repeating step 308 above.

For each of the multiple regions, the system associates the obtained respective image with the position at which the visible marker was displayed to generate (i) a respective calibration image of the user, and (iii) a respective calibration label that labels a known gaze position or region of the user for the calibration image (step 310).

Figure 4:
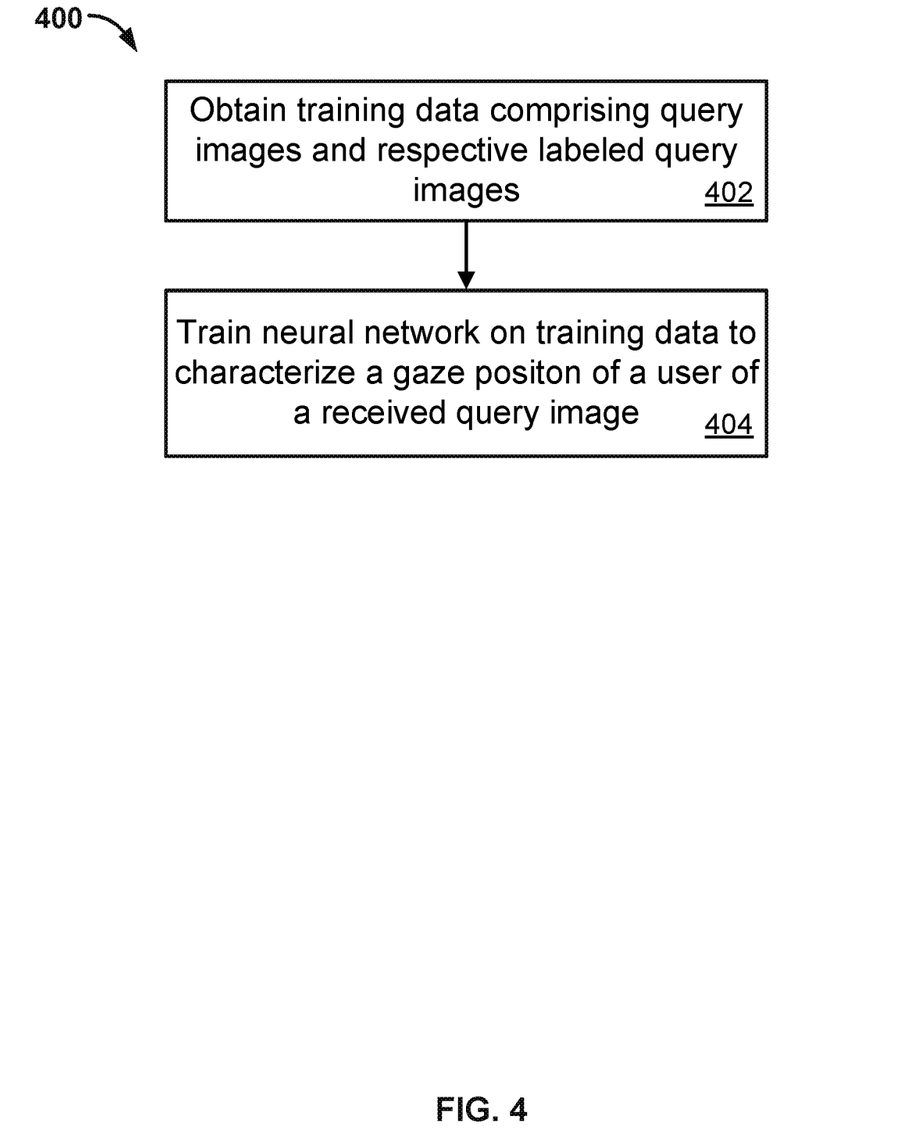
FIG. 4 is a flow diagram of an example process for training a neural network for gaze prediction.

FIG. 4 is a flow diagram of an example process 400 for training a neural network for gaze prediction. For convenience, the process 400 will be described as being performed by a system of one or more computers located in one or more locations. For example, a gaze prediction system, e.g., the gaze prediction system 100 of FIG. 1, appropriately programmed in accordance with this specification, can perform the process 400.

The system obtains training data including, for each of multiple training examples, an aligned training query image and labeled known gaze point for the training query image (step 402). For example, each of the multiple training examples may include a facial image of a user taken from a front facing camera of a user device and a corresponding indication of a gaze point at which it is expected that the user was looking when the facial image was taken, e.g., a gaze point at which the user was actually looking.

The training data may include several thousand training examples, e.g., twelve thousand training examples, which originate from multiple participants, e.g., one hundred participants. In some implementations the training examples may include multiple gaze points per participant and session, e.g., forty gaze points per participant per one minute session, and may include multiple gaze points per participant in a fixed number of sessions, e.g., one hundred and twenty gaze points per participant in three sessions. The training query images may also vary with respect to a pose of a participant, lighting in which the training query image was taken, distance that the training query image was taken from the participant, gender of the participant or ethnicity of the participant. In some implementations the neural network may be trained on training data that includes nine images of a participant, as described above with reference to FIG. 3. For example, the system may obtain a first number of images of each participant corresponding to multiple gaze points, e.g., forty five images. The system may generate a second number of collections of nine images from the first number of images, e.g., five collections of nine images, and train the neural network using the second number of collections.

The system trains the neural network to characterize a gaze position of a user of a received query image on the training data to adjust values of the neural network parameters to determine trained values of the parameters (step 404). For example, for each training query image, the system may process the training query image using the neural network to generate a predicted gaze position, compute a gradient based on a difference between the predicted gaze position and the labeled gaze point for the training query image, i.e., the actual gaze position of the user, and update the values of the neural network parameters by backpropagating the gradient.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory program carrier for execution by, or to control the operation of, data processing apparatus. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them. The computer storage medium is not, however, a propagated signal.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the user device, which acts as a client. Data generated at the user device, e.g., as a result of the user interaction, can be received from the user device at the server.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A gaze prediction system for processing a collection of input facial images of a user to generate a system output that predicts a gaze position of the user, the gaze prediction system comprising:
    an image collection system implemented by one or more computers and configured to:
        obtain one or more calibration images of the user and, for each of the calibration images, a respective calibration label that labels a known gaze position of the user in the calibration image,
        after obtaining the one or more calibration images, obtain a query image of the user, and
        generate a neural network input that includes (i) the query image of the user, (ii) the one or more calibration images of the user, and (iii) the respective calibration labels for the one or more calibration images, and
    a neural network, wherein the neural network is implemented by the one or more computers and comprises one or more neural network layers, and wherein the neural network is configured to, at run time and after the neural network has been trained:
process the neural network input comprising (i) the query image of the user, (ii) the one or more calibration images of the user, and (iii) the respective calibration labels for the one or more calibration images using the one or more neural network layers to generate a neural network output that characterizes a gaze position of the user in the query image.

2. The system of claim 1, wherein the gaze prediction system is implemented on a user device, wherein the user device comprises (i) a display screen, and (ii) a front-facing camera.

3. The system of claim 2, wherein the image collection system obtains the query image of the user using the front facing camera.

4. The system of claim 3, wherein obtaining the one or more calibration images of the user comprises:
determining a size of the display screen;
dividing the display screen into a plurality of regions; and
for each region:
displaying a visible marker in a position within the region of the display screen;
obtaining an image using the front facing camera whilst the visible marker is displayed in the position within the region of the display screen.

5. The system of claim 4, wherein displaying a visible marker in a position within the region of the display screen comprises assigning the position within the region according to a predetermined probability distribution.

6. The method of claim 4, further comprising extracting a facial region of the obtained image to obtain the calibration image.

7. The system of claim 6, wherein extracting a facial region of the obtained image comprises selecting an eye region of the obtained image.

8. The system of claim 4, wherein the image collection system is configured to:
determine whether the obtained image is noisy; and
in response to determining that the obtained image is noisy, reject the obtained image.

9. The system of claim 2, wherein the generated a neural network output that characterizes the gaze position characterizes the gaze position of the user of the user in the query image as a position on the display screen of the user device.

10. The system of claim 1, wherein the one or more calibration images of the user comprises nine calibration images of the user.

11. The neural network of claim 1, wherein the neural network comprises:
a first neural network comprising one or more convolutional layers;
a second neural network comprising one or more fully connected layers;
wherein the first neural network is configured to:
obtain the collection of input facial images of the user;
process the collection of input facial images of the user using the one or more convolutional layers to generate a first neural network output; and
provide the generated first neural network output to the second neural network,
wherein the second neural network is configured to:
receive the generated first neural network output;
process the generated first neural network output using the one or more fully connected layers to generate the neural network system output that characterizes a gaze position of the user in the query image.

12. The system of claim 11, wherein the second neural network comprises two or more fully connected layers configured to
receive the generated first neural network output;
process the generated first neural network output to generate a pair embedding output, wherein the pair embedding output comprises a similarity measure between each of a respective calibration image and the query image.

13. The system of claim 12, wherein the second neural network comprises a fully connected layer that is configured to:
receive the generated pair embedding output;
process the generated pair embedding output to generate an aggregated embedding output, wherein the aggregated embedding output comprises, for each calibration image, a multiplication between a respective calibration image and a pair embedding output.

14. The system of claim 13, wherein the second neural network comprises a fully connected output layer that is configured to:
receive the aggregated embedding output;
process the aggregated embedding output to generate the system output that characterizes a gaze position of the user in the query image.

15. A method for characterizing a gaze position of a user in a query image, comprising:
obtaining one or more calibration images of the user, and, for each of the calibration images, a respective calibration label that labels a known gaze position of the user in the calibration image;
after obtaining the one or more calibration images, obtaining the query image of the user;
generating a neural network input that includes (i) the query image of the user, (ii) the one or more calibration images of the user, and (iii) the respective calibration labels for the one or more calibration images;
processing the neural network input that includes (i) the query image of the user, (ii) the one or more calibration images of the user, and (iii) the respective calibration labels for the one or more calibration images using a neural network, wherein the neural network comprises one or more neural network layers and is configured to, at run time and after the neural network has been trained, process the neural network input using the one or more neural network layers to generate a neural network output that characterizes the gaze position of the user in the query image.

16. The method of claim 15, wherein the obtaining, generating, and processing are performed by a user device, wherein the user device comprises (i) a display screen, and (ii) a front-facing camera.

17. The method of claim 16, wherein the generated neural network output that characterizes the gaze position characterizes the gaze position of the user of the user in the query image as a position on the display screen of the user device.

18. The method of claim 16, wherein obtaining the one or more calibration images of the user comprises:
determining a size of the display screen;
dividing the display screen into a plurality of regions; and
for each region:
displaying a visible marker in a position within the region of the display screen;
obtaining an image using the front facing camera whilst the visible marker is displayed in the position within the region of the display screen.

19. A computer storage medium encoded with instructions that, when executed by one or more computers, cause the one or more computers to perform operations comprising:
- obtaining one or more calibration images of the user, and, for each of the calibration images, a respective calibration label that labels a known gaze position of the user in the calibration image;
- after obtaining the one or more calibration images, obtaining the query image of the user;
- generating a neural network input that includes (i) the query image of the user, (ii) the one or more calibration images of the user, and (iii) the respective calibration labels for the one or more calibration images;
- processing the neural network input that includes (i) the query image of the user, (ii) the one or more calibration images of the user, and (iii) the respective calibration labels for the one or more calibration images using a neural network, wherein the neural network comprises one or more neural network layers and is configured to, at run time and after the neural network has been trained, process the neural network input using the one or more neural network layers to generate a neural network output that characterizes the gaze position of the user in the query image.

* * * * *

UNITED STATES PATENT AND TRADEMARK OFFICE
CERTIFICATE OF CORRECTION

PATENT NO. : 10,127,680 B2
APPLICATION NO. : 15/195942
DATED : November 13, 2018
INVENTOR(S) : Lagun et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 22 days.

Signed and Sealed this
Fourteenth Day of May, 2019

Andrei Iancu
*Director of the United States Patent and Trademark Office*